(12) United States Patent
Shrawat et al.

(10) Patent No.: US 8,895,772 B2
(45) Date of Patent: Nov. 25, 2014

(54) PROCESS FOR PREPARING BICALUTAMIDE

(75) Inventors: Vimal Kumar Shrawat, Karnataka (IN); Karri Papa Rao, Karnataka (IN); Rafiuddin, Karnataka (IN); Prashant Purohit, Karnataka (IN)

(73) Assignee: Shilpa Medicare Limited, Raichur, Karnataka (IN)

( * ) Notice: Subject to any disclaimer, the term of this patent is extended or adjusted under 35 U.S.C. 154(b) by 0 days.

(21) Appl. No.: 13/634,103

(22) PCT Filed: Aug. 29, 2011

(86) PCT No.: PCT/IN2011/000584
§ 371 (c)(1),
(2), (4) Date: Sep. 11, 2012

(87) PCT Pub. No.: WO2012/042532
PCT Pub. Date: Apr. 5, 2012

(65) Prior Publication Data
US 2013/0274501 A1    Oct. 17, 2013

(30) Foreign Application Priority Data

Sep. 29, 2010 (IN) .......................... 2882/CHE/2010

(51) Int. Cl.
| | | |
|---|---|---|
| C07C 381/00 | (2006.01) | |
| C07C 255/50 | (2006.01) | |
| C07C 253/30 | (2006.01) | |
| C07C 315/02 | (2006.01) | |
| C07C 253/34 | (2006.01) | |

(52) U.S. Cl.
CPC ............. C07C 253/30 (2013.01); C07C 315/02 (2013.01); C07C 253/34 (2013.01)
USPC .......................................... 558/413; 564/162

(58) Field of Classification Search
USPC ......................................................... 558/413
See application file for complete search history.

(56) References Cited

U.S. PATENT DOCUMENTS

| | | |
|---|---|---|
| 4,636,505 A | 1/1987 | Tucker |
| 5,985,868 A | 11/1999 | Gray |
| 6,479,692 B1 | 11/2002 | Ekwuribe et al. |
| 6,562,994 B2 | 5/2003 | Chen et al. |
| 6,593,492 B1 | 7/2003 | Ekwuribe et al. |
| 6,737,550 B2 | 5/2004 | Dolitzky et al. |
| 6,740,770 B2 | 5/2004 | Shintaku et al. |
| 6,797,843 B2 | 9/2004 | Dolitzky et al. |
| 6,849,763 B2 | 2/2005 | Dolitzky et al. |
| 6,861,557 B2 | 3/2005 | Dolitzky et al. |
| 7,102,026 B2 | 9/2006 | Dolitzky et al. |
| 7,132,560 B2 | 11/2006 | Shintaku et al. |
| 7,199,257 B1 | 4/2007 | Soros et al. |
| 2003/0045742 A1 | 3/2003 | Ekwuribe |
| 2003/0073742 A1 | 4/2003 | Thijs et al. |
| 2004/0133031 A1* | 7/2004 | Shintaku et al. .............. 558/413 |
| 2004/0167349 A1 | 8/2004 | Dolitzky et al. |
| 2005/0090682 A1 | 4/2005 | Dolitzky et al. |
| 2006/0079706 A1* | 4/2006 | Parthasaradhi et al. ....... 558/413 |

FOREIGN PATENT DOCUMENTS

| | | |
|---|---|---|
| CN | 1458146 A * | 11/2003 |
| EP | 0100172 | 2/1984 |
| WO | WO0100608 | 1/2001 |
| WO | WO0134563 | 5/2001 |
| WO | WO0224638 | 3/2002 |
| WO | WO02100339 | 12/2002 |
| WO | WO03053920 | 7/2003 |
| WO | WO 2009087666 A2 * | 7/2009 |

OTHER PUBLICATIONS

Tucker et. al. Synthesis and Structure-Activity Relationships of 3-Substituted Derivatives of 2-Hydroxypropionanilides J. med. Chem, 31, 9-954-959 (1988).

* cited by examiner

Primary Examiner — Nyeemah A Grazier

(57) ABSTRACT

The present invention provide processes for the preparation of N-[4-Cyano-3-(trifluoro methyl)phenyl]-3-[(4-fluorophenyl)sulphonyl]-2-hydroxy-2-methyl propanamide (I).

The present application also provides a method of purification of N-[4-Cyano-3-(trifluoro methyl)phenyl]-3-[(4-fluorophenyl)sulphonyl]-2-hydroxy-2-methyl propanamide (I) using ethyl acetate solvent resulting in the product, substantially free from process related impurities A, B, C and D. The crystalline product of the process according to the present invention having an XRDP pattern as per FIG. 1, is useful as an active pharmaceutical and has anti-androgenic activity.

9 Claims, 6 Drawing Sheets

PROCESS FOR PREPARING BICALUTAMIDE

FIELD OF THE INVENTION

Particular aspects of the present application relate to a process for preparation of bicalutamide.

BACKGROUND OF THE INVENTION

Bicalutamide is the generic name for the compound N-[4-Cyano-3-(trifluoromethyl)phenyl]-3-[(4-fluorophenyl)sulphonyl]-2-hydroxy-2-methyl propanamide and is represented by the formula (I)

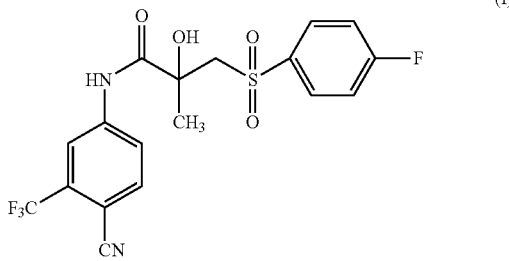

Bicalutamide and related various acyl anilides have been disclosed in U.S. Pat. No. 4,636,505 as pharmaceutically active compounds possessing anti-androgenic activity useful in the treatment of prostate cancer. The pharmaceutical product derived from Bicalutamide is approved worldwide under the brand name Casodex.

Process for preparing Bicalutamide has been reported in U.S. Pat. No. 4,636,505 issued to ICI and Tucker et. al. in J. med. Chem, 31, 9-954-959 (1988) by reacting 3-Trifluoromethyl-4-cyanoaniline of Formula (IV) with methacryloyl chloride of Formula (III) followed by epoxidation of the resultant N-(3-trifluoromethyl-4-cyanophenyl)methacrylamide of Formula (V). The epoxide ring is opened with 4-fluorothiophenol and subsequent conversion to sulfone resulted in Bicalutamide of Formula (I).

Bicalutamide is a non-steroidal pharmaceutically active agent possessing antiandrogenic properties, generally used in treatment of prostate cancer i.e. for androgen deprivation treatment, although other androgen dependent conditions may also be treated. Bicalutamide is commercially available in a pharmaceutical composition as a racemate under the brand name Casodex (Astra-Zeneca). The stereoisomer of Bicalutamide has been proposed in U.S. Pat. No. 5,985,868 as being more beneficial than the racemate. Various other methods for the preparation for Bicalutamide are disclosed in WO0224638, U.S. Pat. No. 6,479,692, WO02100339, US20030073742 and US20030045742.

Though there are several methods known in the art for making N-[4-Cyano-3-(trifluoromethyl)phenyl]-3-[(4-fluorophenyl)sulphonyl]-2-hydroxy-2-methyl propanamide i.e Bicalutamide from its precursor (VII) i.e. N-[4-cyano-3-(trimethyl)phenyl]-3-[(4-fluorophenyl)thio]-2-hydroxy-2-methyl propanamide (VII) by oxidation, however, involves the use of different oxidizing agents including various peracids.

WO0224638 discloses the above oxidation using 30% $H_2O_2$ in presence of trifluoro acetic anhydride in methylene dichloride ($CH_2Cl_2$) at 25° C. to 30° C.

WO0353920 claims oxidation process of N-[4-cyano-3-(trimethyl)phenyl]-3-[(4-fluorophenyl)thio]-2-hydroxy-2-methyl propanamide (VII) using $H_2O_2$/Sodium tungstate/Phenyl phosphoric acid/TBAB/Ethyl acetate.

EP0100172, WO0134563, WO02100339 and Tucker et al in J. Med. Chem. 954-959 disclose the oxidation of N-[4-cyano-3-(trimethyl)phenyl]-3-[(4-fluorophenyl)thio]-2-hydroxy-2-methyl propanamide(VII) using m-chloro perbenzoic acid (m-CPBA) in chlorinated solvent, that requires longer durations for reaction. Thus, the process disclosed in the prior art not only involves the use of expensive reagents and chlorinated solvents, but also their handling and risk concerns while handing them at commercial scales. Chlorinated solvents are particularly known to be harmful to humans with a suggested possibility of being carcinogenic and also produce dioxin during disposal. Further solvents like $CH_2Cl_2$ involves higher cost of disposal due to corrosion during incineration.

Further the chemical risk reduction policy, "Green Chemistry" is gaining attention and industrially feasible environment friendly chemical reactions (avoiding, as far as possible, the use of harmful chemicals and developing reactions which do not as far as possible discharge these) are becoming an essential feature in research. The above-mentioned reaction using $CH_2Cl_2$ as organic solvent is from this point of view not suited for the method of preparation of the desirable Bicalutamide.

Besides being an expensive reagent, MCPBA is a highly explosive material and therefore not suitable for industrial level productions.

One such synthesis of Bicalutamide without the use of m-CPBA is published in WO0100608, which involves the use of an aqueous solution of $H_2O_2$ and the compound is oxidized in acetic or formic acid and is considered as an excellent industrial method environmentally and economically for conversion of Formula (VII) to Formula (I). However in this method, both polar and non-polar impurities are formed which are not reduced during purification. Further this method also has a step involving use of halogenated organic solvent (e.g. 1,1,1-trichloro ethane) for the synthesis of (VI) and so cannot be considered environmentally friendly.

Further in WO0224638, $H_2O_2$ aqueous solution is added to compound of Formula (VII) and the mixture after cooling to −55° C., anhydrous trifluoro acetic acid (TFA) is added to the mixture to get Bicalutamide. But in this method the use of explosive TFA as reagent and the need for cooling during the addition of TEA makes the method uneconomical. Further anhydrous TFA is corrosive and hygroscopic.

WO03053920 has claimed the process of oxidation using $H_2O_2$/Sodium tungstate/Phenyl phosphoric acid/TBAB/Ethyl acetate in good yield. Here the large excess of $H_2O_2$ (3 to 6 equivalents) per mole equivalent of the compound of Formula (VII) and use of large quantity of Sodium tungstate or phenyl phosphoric acid, 0.5 to 5% quantity of compound. Further removal of Sodium tungstate and Phenyl phosphoric acid from the reaction mixture is tedious.

Despite the aforementioned various disclosures mentioning various processes, there still remains a need for new economically viable process and amenable to industrial scale up.

Hence, the present specification is aimed to provide an improved process for the synthesis of Bicalutamide in high yield and purity, which involves the use of inexpensive, non-hazardous and easily available oxidizing agent.

SUMMARY OF THE INVENTION

Particular aspects of the present specification relate to the processes for preparation of Bicalutamide.

In an aspect, the present invention provides a process of preparation of N-[4' cyano 3'-(trifluoromethyl)phenyl]-3-[(4"-fluoro-phenyl)sulfonyl]-2-hydroxy-2-methylpropionamide (I) or Bicalutamide—

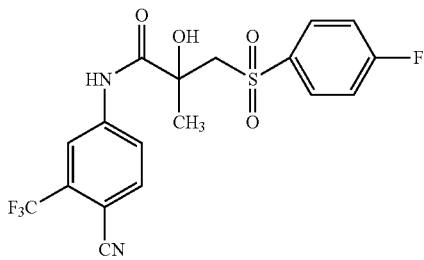

(I)

comprising the steps of— a. Selectively Oxidizing N-[4'-Cyano-3'-(trifluoromethyl) phenyl]-3-[(4"-fluoro phenyl)thio]-2-hydroxy-2-methyl propionamide of Formula (III)—

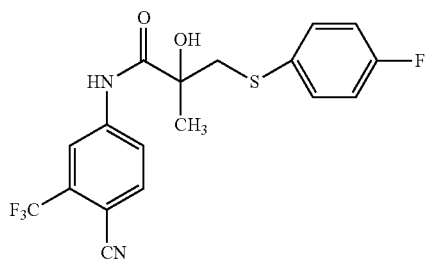

(III)

in presence of an C1-C3 organic alcohol solvent, 1% aqueous ortho tungstic acid and aqueous hydrogen peroxide b. Raising the temperature upto about 50° C. or more and maintaining the temperature while stirring until the content of compound of formula (III) achieved till less than about 1%.

c. Cool the reaction mass and isolating the solid.

d. Add mixture of water and water immiscible ester solvent in a ratio of about 1:2 v/v.

e. Separate the organic ester solvent layer.

f. Optionally repeat the further extraction of aqueous layer with water immiscible ester solvent g. Optionally adding activated carbon followed by filtering the extracted organic layer h. Evaporating the water immiscible ester solvent i. Isolating the compound of formula (I)

In another aspect, the present invention provides process of preparation of N-[4'-cyano-3'-(trifluoro methyl)phenyl]-3-[(4"-fluoro-phenyl)sulfonyl]-2-hydroxy-2-methylpropionamide (I) or bicalutamide

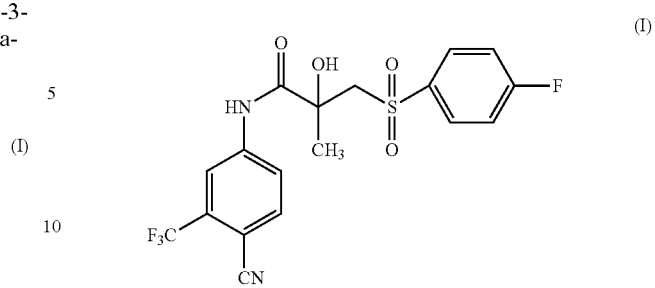

(I)

comprising the steps of— a. Selectively Oxidizing N-[4'-Cyano-3'-(trifluoromethyl) phenyl]-3-[(4"-fluoro phenyl)thio]-2-hydroxy-2-methyl propionamide of Formula (III)—

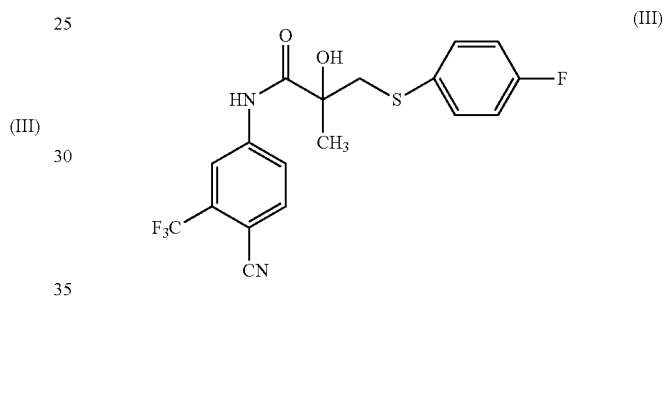

(III)

with aqueous hydrogen peroxide in presence of a non-halogenated organic acid solvent.

b. Admixing the reaction mass of step a) with aqueous sodium bicarbonate solution followed by stirring for duration upto at least 30 minutes c. Extract the reaction mass with water immiscible ester solvent d. Optionally adding activated carbon followed by filtering the extracted organic layer e. Evaporating the water immiscible ester solvent f. Isolating the compound of formula (I)

In yet another aspect, the present invention provides process for purification comprising mixing bicalutamide (I) with ethyl acetate and heating the solution containing Bicalutamide up to at least about 50° C. followed recovering ethyl acetate and isolating the product having an X-ray diffraction pattern substantially similar to as given in FIG. 1.

In a further another aspect, the present invention provides N-[4'-cyano-3'-(trifluoro methyl)phenyl]-3-[(4"-fluoro-phenyl)sulfonyl]-2-hydroxy-2-methylpropionamide (I) or Bicalutamide substantially free from impurities A, B, C and D.

(A) 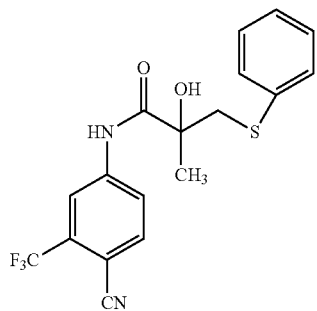

(B) 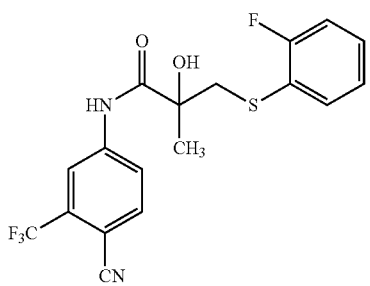

(C) 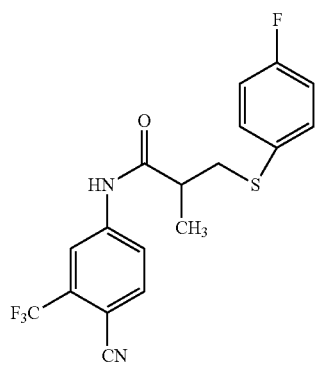

(D) 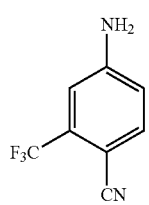

wherein substantially free from impurities has meaning of individual at least any of the three impurities are either not detectable or if present, their individual contents are below 0.05% w/w and a total of all four impurities not exceeding 0.1% w/w.

DETAILED DESCRIPTION OF THE INVENTION

Figure 1:
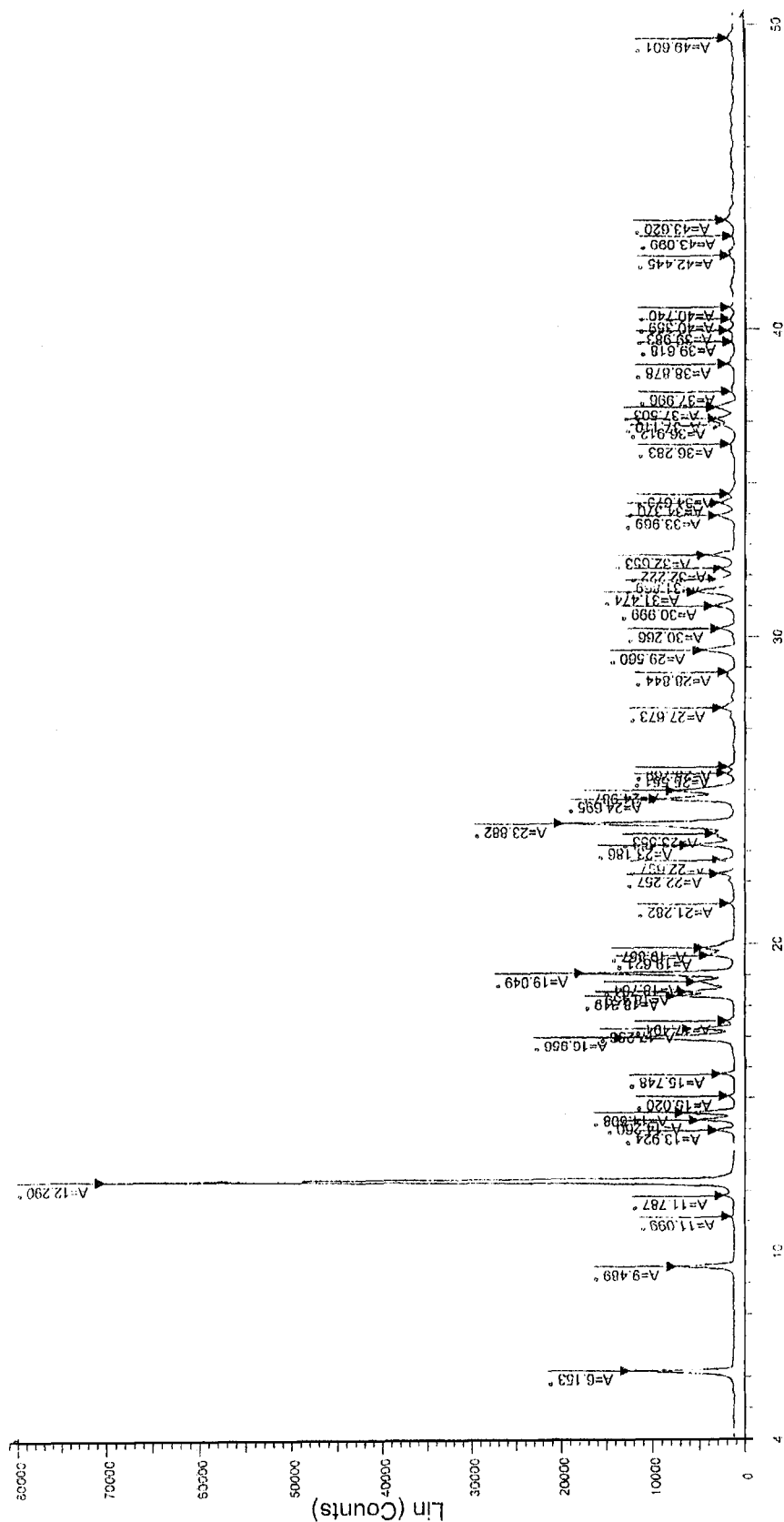
FIG. 1 is an example of an X-ray powder diffraction (XRPD) pattern of Bicalutamide, prepared according to Example-Stage-B1

As set forth herein, aspects of the present invention relate to the processes for preparation of Bicalutamide.

In one embodiment of the present application, it provides a process of preparation of N-[4'-cyano-3'-(trifluoro methyl) phenyl]-3-[(4"-fluoro-phenyl)sulfonyl]-2-hydroxy-2-methyl propionamide (I) or Bicalutamide—

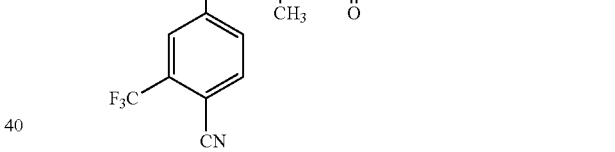

comprising the steps of—
a. Selectively Oxidizing N-[4'-Cyano-3'-(trifluoromethyl) phenyl]-3-[(4"-fluoro phenyl)thio]-2-hydroxy-2-methyl propionamide of Formula (III)—

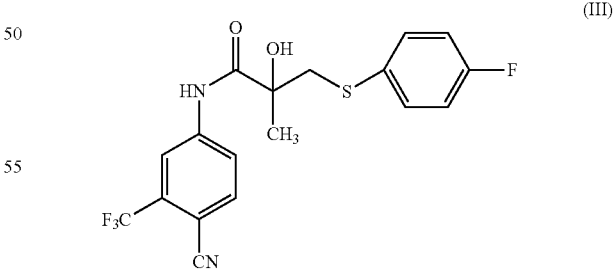

in presence of an C1-C3 organic alcohol solvent, 1% aqueous ortho tungstic acid and aqueous hydrogen peroxide
b. Raising the temperature upto about 50° C. or more and maintaining the temperature while stirring until the content of compound of formula (III) achieved till less than about 1%.
c. Cool the reaction mass and isolating the solid.

d. Add mixture of water and water immiscible ester solvent in a ratio of about 1:2 v/v.
e. Separate the organic ester solvent layer.
f. Optionally repeat the further extraction of aqueous layer with water immiscible ester solvent
g. Optionally adding activated carbon followed by filtering the extracted organic layer
h. Evaporating the water immiscible ester solvent
i. Isolating the compound of formula (I)

The Selectively Oxidizing in the present process of the invention comprising only the selective oxidation of sulphur atom present on compound of formula-III, wherein the other oxidation prone sites like —CN, —$CH_3$, —CH—OH group remained unaffected while carrying out the oxidation utilizing the specific selected and easily available oxidizing agents and performing a large scale well controlled user and environment friendly process resulting not only good yields but also making the process industrially viable.

The C1-C3 organic alcohol solvent utilized in the process of the present invention includes alcohols selected from methanol, ethanol, n-propanol and isopropanol or mixtures thereof.

Use of 1% aqueous ortho tungstic acid is specific requirement for the process, however, said solution may be having varying strengths ranging between 0.5% to 2% and construed to be within the scope of the said process. The addition of aqueous ortho tungstic acid solution is carried out at room temperature, however, the temperature of addition comprising a range between 10-30° C.

Addition of hydrogen peroxide in strengths comprising ranging between 20-35% solution is usually preferred and a slow addition mode for the hydrogen peroxide is preferred, which may be 1-3 gm of the aqueous peroxide solution per minute in a reaction mass at a temperature ranging between about 5-15° C. For example, if about 40 gm of peroxide solution is to be added, it may take time ranging between 40 minutes to 120 minutes in order to achieve the well controlled reaction kinetics. A quicker addition may be deleterious to the reaction and similarly extremely low temperatures of the reaction mass may freeze and slow down the reaction exceptionally.

Once the peroxide solution was added completely, a controlled rising of the temperature up to about 50° C. or more and maintaining the temperature while stirring until the content of compound of formula (III) achieved till less than about 1% is also one of the principal requirement of the invention as per the present application.

In one of the preferred embodiment, the temperature was slowly raised up to about 60-65° C. and maintained for about 3-4 hours under continuous stirring. For this step, monitoring of the selective oxidation reaction was carried by HPLC in order to ensure the selective oxidation and the unreacted raw material i.e. compound of formula (III) shall be less than about 0.5% w/w (By HPLC).

After achieving this selective oxidation, the reaction mixture is cool preferably up to 0-5° C. and retain this temperature for about one hour. This is in order to ensure the maximum possible out put from the reaction mass.

Isolation of the solid material may be carried out by techniques known to the person having ordinary skill in the art.

Further steps of addition of water and water immiscible ester solvent in a ratio of about 1:2 v/v to the solid may be carried out to ensure the removal of water soluble impurities. Ratio of about 1:2 v/v water and water immiscible ester solvent is preferred in view of adequate desired purification, however, this ratio may extend up to 1:2 to 5 volumes of ester solvent as long as it is able to provide handing and volume needs user friendly and the product obtained is acceptable.

In one of the preferred embodiment, the preferred ester solvent was Ethyl acetate and ratio of ethyl acetate and water remained nearly 2:1.

After addition of water to the solid material, it was stir for suitable time durations, which may range between 30 minutes to 120 minutes in order to achieve layer separation. Once the stirring is stopped and the ester solvent layer was separated. The remaining aqueous layer was extracted by using the same ester solvent, which may be repeated again, if the product contents are still present in the aqueous layer, without compromising the water soluble impurities.

The ester solvent layers may be pooled and subjected for removal of moisture content present in the ester solvent layer by addition of suitable amount of anhydrous sodium sulfate.

Optional addition of activated carbon may also be carried out in order to remove any colored impurities present in the ester solvent layer, which is stirred for duration ranging between 15 minutes to about 60 mins and subjected to filter through hyflow bed.

Recovery of ester solvent may be carried out up to an extent, when ester solvent remained in the ratio of 1.0-2.0 ml/gm of the reaction mass, which may be measured based on the initially taken crude product—Bicalutamide and the recovered solvent quantity. For example, if the 50 gm crude Bicalutamide was taken initially and 550 ml ester solvent was added into it, and recovered ester solvent quantity was in between about 450 to 500 ml, the approximate solvent remained in the ratio of 1.0-2.0 ml/gm of the reaction mass or 50 ml-100 ml per 50 gm of the input crude Bicalutamide.

The recovery of the ester solvent is one of the specific inventive aspects of the present invention and is carried out under reduced pressures in order to maintain the temperatures ranging between 30-50° C.

Once the desired amount of the ester solvent was recovered, the reaction mass was cooled to a temperature ranging between 0-5° C. and this temperature was maintained for about 1-2 hours. The solid material was filtered and finally washed with chilled ethyl acetate and later on subjected to drying.

In one of the preferred embodiment, the drying of the material was carried out at temperature ranging between about 45-65° C. under vacuum for 8-10 hours, however, drying may be stopped prior also, once the water content is achieved upto about less than 0.20% w/w.

The details of the process as per this embodiment are delineated in the scheme-1 and example B1 and their specifics demonstrated in the example may not be construed to limit the scope of the present invention.

The product obtained from the process of the present invention provides Bicalutamide, which is substantially free from impurities A, B C and D.

(A) 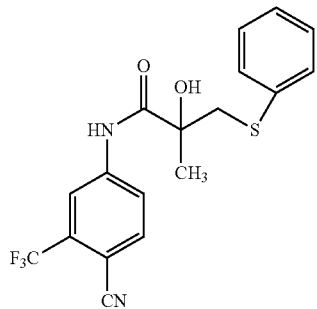

(B) 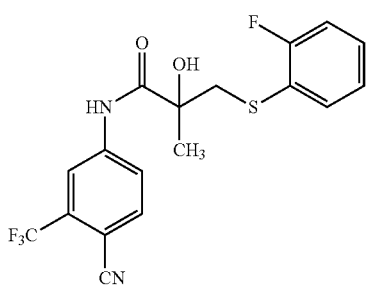

(C) 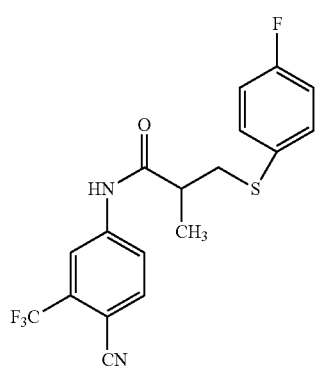

(D) 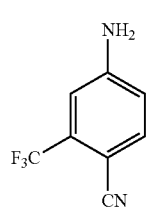

For clarity, substantially free from impurities has meaning of individual at least any of the three impurities are either not detectable or if present, their individual contents are below 0.05% w/w and a total of all four impurities not exceeding 0.1% w/w.

In another embodiment, the present invention provides process of preparation of N-[4'-cyano-3'-(trifluoro methyl) phenyl]-3-[(4"-fluoro-phenyl)sulfonyl]-2-hydroxy-2-methylpropionamide (I) or bicalutamide

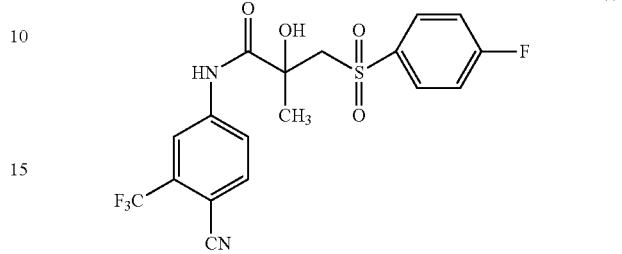

Comprising the steps of— a. Selectively Oxidizing N-[4'-Cyano-3'-(trifluoromethyl) phenyl]-3-[(4"-fluoro phenyl)thio]-2-hydroxy-2-methyl propionamide of Formula (III)—

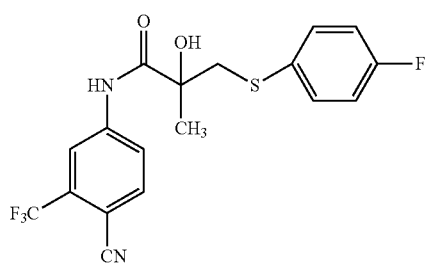

with aqueous hydrogen peroxide in presence of a non-halogenated organic acid solvent.

b. Admixing the reaction mass of step a) with aqueous sodium bicarbonate solution followed by stirring for duration upto at least 30 minutes c. Extract the reaction mass with water immiscible ester solvent d. Optionally adding activated carbon followed by filtering the extracted organic layer e. Evaporating the water immiscible ester solvent f. Isolating the compound of formula (I)

The details of the process as per this embodiment are delineated in the scheme-1 and example B2 and their specifics demonstrated in the example may not be construed to limit the scope of the present invention.

Scheme-I: Preparation of Bicalutamide as per the present invention
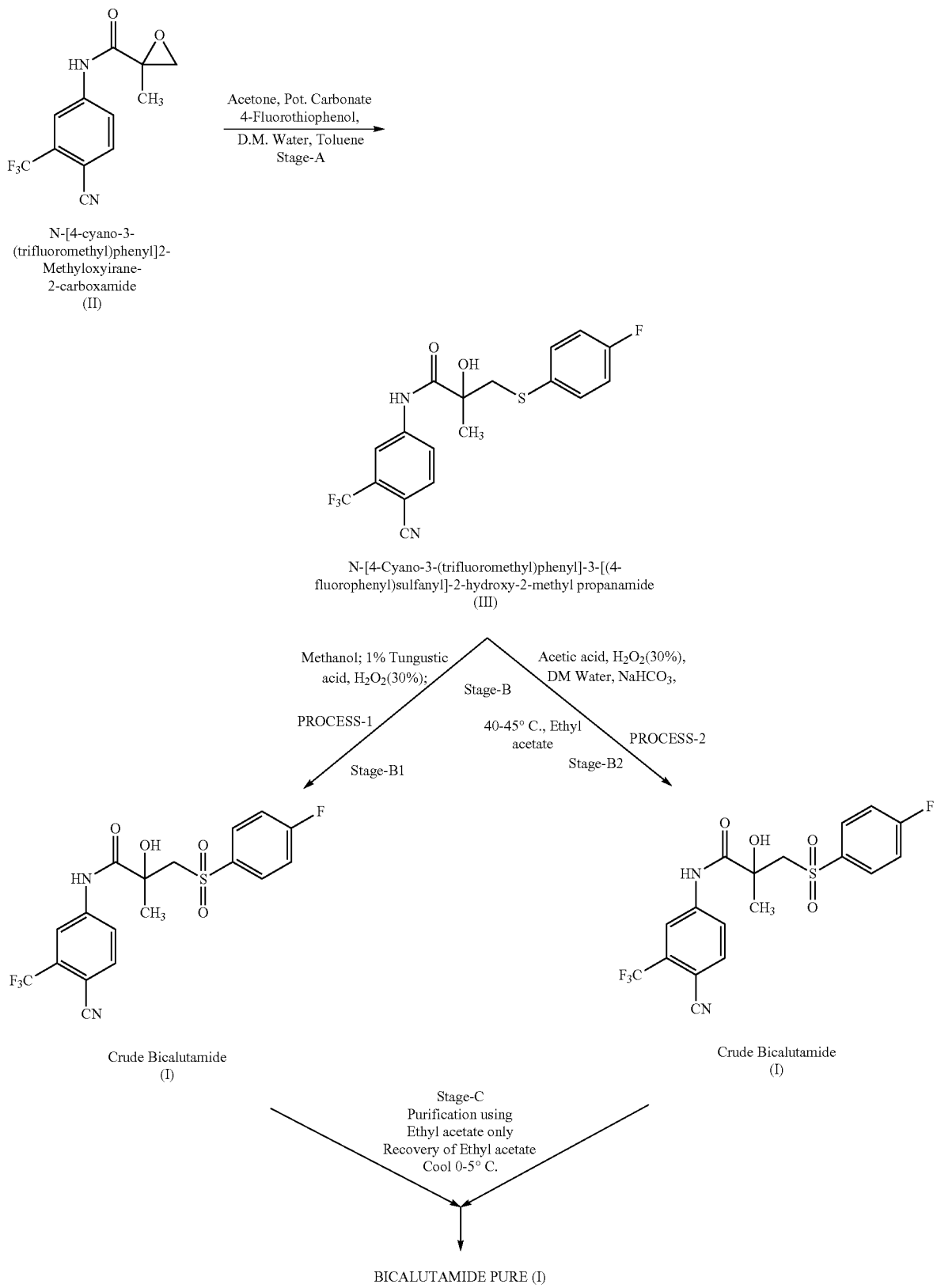

Crystalline Bicalutamide obtained by both the processes (Process B1 and B2—As per Scheme-I) of the present inventions results in the characteristic polymorphic form XRPD pattern, which is designated as "Form S". A polymorphic form may be described by reference to patterns, spectra, or other graphical data as "substantially" shown or depicted in a figure, or by one or more data points. It will be appreciated that patterns, spectra, and other graphical data may be slightly shifted in their positions, relative intensities, or other values due to various factors known to the person skilled in the art. For example, in the crystallographic and powder X-ray diffraction science, shifts in peak positions or the relative intensities of one or more peaks of a pattern can occur because of, the equipment used, protocol of the sample preparation, preferred packing and orientations, the radiation source, operator's minor operational error, method and length of data collection, and the like.

However, those of ordinary skill in the art will be able to compare the figures herein with patterns, etc. generated for an unknown form of, in this case, Bicalutamide, and confirms its identity with "Form S" disclosed herein. The same holds true for other techniques which may be reported herein.

Bicalutamide "Form S" obtained by the process of present application is characterized by its X-ray powder diffraction ("XRPD") pattern, differential scanning calorimetry ("DSC") curve, and FT-IR spectra data.

In addition, where a reference is made to a figure, it is permissible to, and this document includes and contemplates, the selection of any number of data points illustrated in the figure that uniquely define that crystalline form, within any associated and recited margin of error, for purposes of identification.

All percentages and ratios used herein are by weight of the total composition and all measurements made are at about 25° C. and about normal pressure, unless otherwise designated. All temperatures are in degrees Celsius unless specified otherwise. As used herein, "comprising" (open ended) means the elements recited, or their equivalent in structure or function, plus any other element or elements which are not recited. The terms "having" and "including" are also to be construed as open ended. As used herein, "consisting essentially of" means that the invention may include ingredients in addition to those recited in the claim, but only if the additional ingredients do not materially alter the basic and novel characteristics of the claimed invention. All ranges recited herein include the endpoints, including those that recite a range "between" two values. Whether so indicated or not, all values recited herein are approximate as defined by the circumstances, including the degree of expected experimental error, technique error, and instrument error for a given technique used to measure a value.

In another embodiment, the invention also provides the process for purification of N-[4-Cyano-3-(trifluoromethyl) phenyl]-3-[(4-fluorophenyl)sulphonyl]-2-hydroxy-2-methyl propanamide (I) comprising mixing bicalutamide (I) with ester solvent and heating the solution containing Bicalutamide up to at least about 50° C. or more followed recovering ester solvent and isolating the product having an X-ray diffraction pattern substantially similar to as given in FIG. 1.

Mixing of Bicalutamide (I) with ester solvent may be achieved direct from the inprocess or insitu reaction solutions or it may be carried out in isolation, wherein the crude bicalutamide obtained by any processes including those disclosed in patents WO0224638, WO0100608, WO03053920 and U.S. Pat. No. 4,636,505, all of which are incorporated by reference in their entirety herein.

In one of the preferred embodiment, the heating of solution carried out up to 60-65° C. in order to provide the clear solution.

The ester solvent utilized in process for purification of the present invention comprising the organic esters having C2 to C6 carbon atoms in total. A few organic esters which may be used includes—methyl acetate, ethyl acetate, propyl acetate etc. or mixtures thereof.

It is also preferable to get the desired crystalline Form-S of the present invention by keeping the moisture content as minimum as possible in the ester solvent, preferably less than 0.5% w/w.

The recovery of the ester solvent is one of the specific inventive aspects of the present invention and is carried out under reduced pressures in order to maintain the temperatures ranging between 30-50° C.

The extent of recovery of solvent is also one of the critical factors to get the crystalline form—"Form-S" of the present invention, which is stable at room temperatures. Recovery of solvent upto an extent, when ester solvent remained in the ratio of 1.0-2.0 ml/gm of the reaction mass, which may be measured based on the initially taken crude product—Bicalutamide and the recovered solvent quantity. For example, if the 50 gm crude Bicalutamide was taken initially and 550 ml ester solvent was added into it, and recovered ester solvent quantity was in between about 450 to 500 ml, the approximate solvent remained in the ratio of 1.0-2.0 ml/gm of the reaction mass or 50 ml-100 ml per 50 gm of the input crude Bicalutamide.

The present invention describes a process for preparing N-[4-Cyano-3-(trifluoromethyl)phenyl]-3-[(4-fluorophenyl) sulphonyl]-2-hydroxy-2-methyl propanamide of formula (I)—crystalline "Form S", known as Bicalutamide. However, the inventive crystalline form—"Form S" can also prepared from any compound within the scope of formula (I) including those disclosed in patents WO0224638, WO0100608, WO03053920 and U.S. Pat. No. 4,636,505, all of which are incorporated by reference in their entirety herein.

In a further embodiment, the present invention provides N-[4'-cyano-3'-(trifluoro methyl)phenyl]-3-[(4"-fluoro-phenyl)sulfonyl]-2-hydroxy-2-methylpropionamide (I) or Bicalutamide substantially free from impurities A, B, C and D, which presented below.

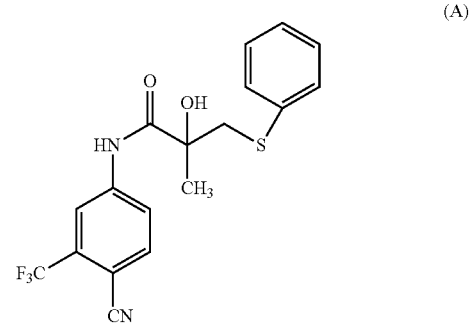

(A)

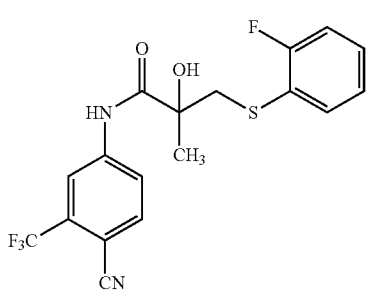
(B)

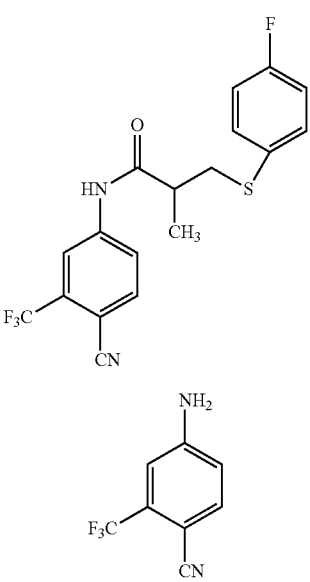
(C)

(D)
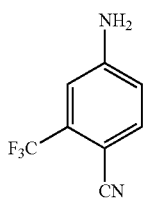

The product of the present invention provides Bicalutamide, which is substantially free from impurities A, B C and D. For clarity, substantially free from impurities has meaning of individual at least any of the three impurities are either not detectable or if present, their individual contents are below 0.05% w/w and a total of all four impurities not exceeding 0.1% w/w.

The crystalline solid (referred to as 'Form S') exhibits an X-ray powder diffraction pattern substantially as shown in FIG. 1. The prominent and characteristic 2θ° and 'd' spacing values for the Form-S of the present invention, includes 6.1 (14.40 d value), 12.2 (7.20 d value), 16.9 (5.23 d value), 19.0 (4.65 d value), 23.8 (3.72 d value), 24.9 (3.56 d value), 29.5 and 31.5±0.2 (±0.1 d value).

The crystalline solid 'Form S' described herein may be characterized by X-ray powder diffraction pattern (XRPD), Thermal techniques such as differential scanning calorimetry (DSC) and IR spectral Analysis. X-Ray powder diffraction pattern were collected on a Brukar AXS D 8 advance Diffractometer using Cu Kα1 (wavelength 1.5418 Å) radiation (40 kV, 30 mA), automated XYZ stage, divergence, receiving slits and PSD lynx Eye detector. Sample was run under ambient condition.

Illustrative examples of analytical data for the crystalline solid 'Form S' obtained in the Examples are set forth in the FIGS. 1-5.

In another embodiment, the crystalline "Form S" of Bicalutamide obtained by the process of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising Crystalline Form-S of Bicalutamide of the present application include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions of Crystalline Form-S of Bicalutamide of the present application may also comprise to include the pharmaceutically acceptable carrier used for the preparation of solid dispersion, wherever utilized in the desired dosage form preparation.

Certain specific aspects and embodiments of the present application will be explained in more detail with reference to the following examples, which are provided by way of illustration only and should not be construed as limiting the scope of the invention in any manner.

EXAMPLE

Preparation of N-[4-Cyano-3-(trifluoromethyl)phenyl]-3-[(4-fluorophenyl)sulphonyl]-2-hyd-roxy-2-methyl propanamide (Bicalutamide)

The process for the preparation of Bicalutamide comprises of following three stages, namely A, B and C. Individual stages A, B and C are provided separately herein below—

Stage A). Preparation of N-[4-Cyano-3-(trifluoromethyl)phenyl]-3-[(4-fluorophenyl)sulfanyl]-2-hydroxy-2-methyl propanamide (2)

250 ml of Acetone and 25 gm of N-[4-cyano-3-(trifluoromethyl)phenyl] 2-Methyloxirane-2-carboxamide (1) charged into a 500 ml flask at room temperature under stirring and stirred till to obtain the clear solution. 9.8 gm of Potassium Carbonate was added and cooled the reaction mixture to 10-15° C. under stirring.

Added 15 gm 4-Fluorothiophenol slowly through addition tank in 3-4 hours at 10-15° C. under stirring. Removed the cooling and brought the reaction mixture to RT under stirring and stirred for 2-3 hours at RT while monitoring the reaction by HPLC for the presence of unreacted—N-[4-cyano-3-(trifluoro methyl)phenyl] 2-Methyloxirane-2-carboxamide (1) (unreacted compound (I)<0.50%].

Filter the reaction mixture over Nutsche Filter and wash with 50 ml acetone. Acetone was later on recovered completely at 40-50° C. under vacuum until dryness. To this dried residue, 250 ml DM water was added and stirred the solution for 4-5 hours at RT. About 125 ml Toluene was added to this solution and stirred the reaction mixture for 10-12 hours. The reaction mixture was filtered and washed with 50 ml Toluene. The solid was dried for 6-7 hours under vacuum. 34 gm solid was obtained; Yield—92.5%, Water content—0.2% w/w; Purity—99.0% by HPLC.

Stage B: It May be Either Stage B1 or B2, However, Both the Processes are Part of the Present Invention of this Application. Any of the Stage B1 or B2 Process May be Used for the Preparation Crude Bicalutamide (3)

Stage B1). Preparation of N-[4-Cyano-3-(trifluoro methyl)phenyl]-3-[(4-fluorophenyl)sulfonyl]-2-hydroxy-2-methylpropanamide or Crude Bicalutamide (3)

Charged 250 ml Methanol into a reaction flask at room temperature under stirring then added 25 gm N-[4-Cyano-3-(trifluoromethyl)phenyl]-3-[(4-fluorophenyl)sulfanyl]-2-hydroxy-2-methyl propanamide (2). The mixture was continued to stir for 30 min at room temperature in order to obtain the clear solution. Then added 1.0% Tungstic acid at room temperature under stirring and cooled the reaction mixture up to 10-15° C. Start adding slowly added 43 gm, 30% solution of Hydrogen peroxide in 1-2 hrs. Raised the temperature to 60-65° C. and maintained this temperature for 3-4 hrs under stirring. Cooled the reaction mixture to 0-5° C. and maintained for one hour. Filtered the solid material and washed with 10 ml methanol and suck dried the material. 330 ml Ethyl acetate and 110 ml water added to the solid material and stirred for 30 min then stop stirring and separated the Ethyl acetate layer.

Again charged the Ethyl acetate layer and washed with 110 ml DM water and separated the Ethyl acetate layer. In order to make the Ethyl acetate layer moisture free, 10.0 gm anhydrous sodium sulphate was added and followed by about. 2.1 gm activated carbon and stirred for one hour then filtered through hyflow bed (10 gm). Recovered the ethyl acetate solvent at 50° C. and left the solvent about level of 1 ml/g.

Cooled down the reaction mass to 0-5° C. and maintained this temperature for 1-2 hrs. Filtered the solid material and finally wash with about 5 ml chilled ethyl acetate.

Dried the material at 45-65° C. under vacuum for 8-10 hrs. 17 gm solid was obtained; Yield of 68.75%, Water content <0.2% w/w; Purity—99.94% (by HPLC).

Process related impurities A—nil %; B—0.01%; C—nil % and D—nil %

Figure 2:
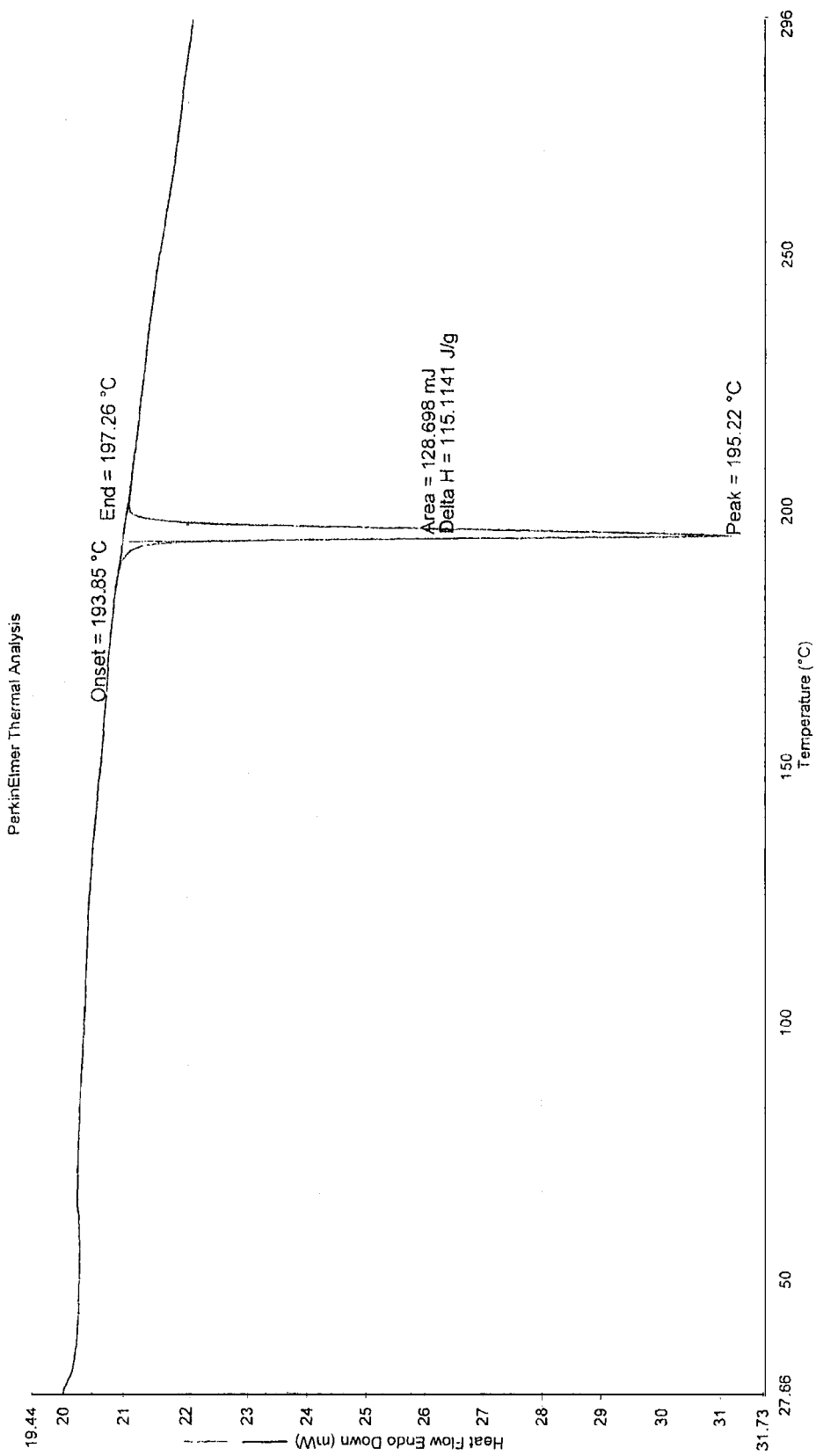
FIG. 2 is an example of a differential scanning calorimetry ("DSC") curve of Bicalutamide, prepared according to Example-Stage-V.
Figure 3:
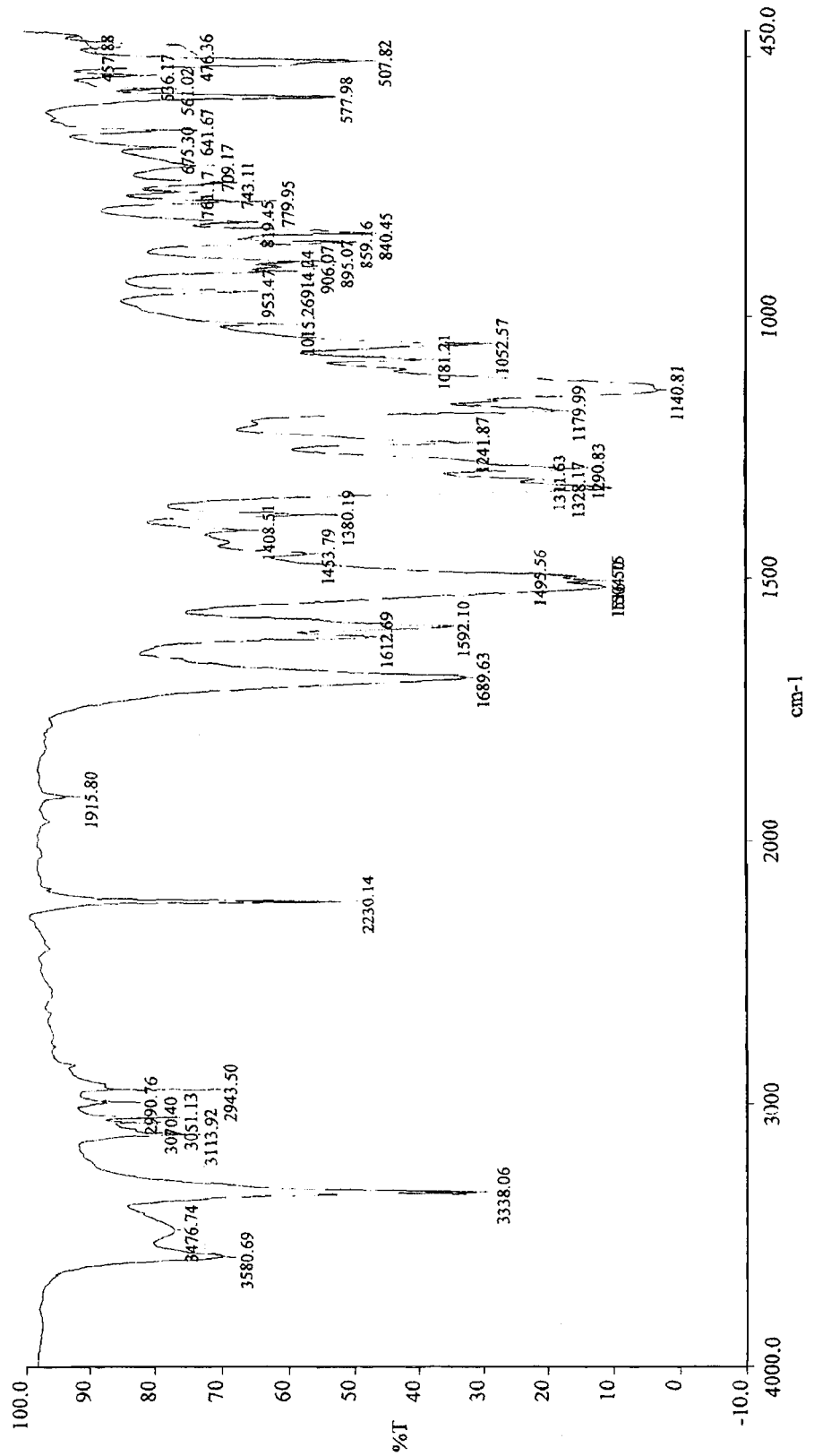
FIG. 3 is an example of a FT-IR of Bicalutamide, prepared according to Example-Stage-B1.

XRPD Pattern as per FIG. 1
DSC thermogram as per FIG. 2
IR Spectra as per FIG. 3

Alternatively, the process of the present invention involves the other industrially viable process approach, which is given as Stage B2.

Stage B2). Preparation of N-[4-Cyano-3-(trifluoromethyl)phenyl]-3-[(4-fluorophenyl)sulfonyl]-2-hydroxy-2-methylpropanamide or Crude Bicalutamide (3)

Charged 50 L of Acetone and 5 kg of N-[4-cyano-3-(trifluoromethyl)phenyl] 2-Methyloxirane-2-carboxamide (1) into a SS reactor at room temperature under stirring and stirred till to obtain the clear solution. 1.96 kg of Potassium Carbonate was added under stirring and cooled the reaction mixture to 10-15° C. under stirring.

Added 3.0 kg 4-Fluorothiophenol slowly through addition tank in 3-4 hours at 10-15° C. under stirring. Removed the cooling and brought the reaction mixture to RT under stirring and stirred for 5-6 hours at RT while monitoring the reaction by HPLC for the presence of unreacted—N-[4-cyano-3-(trifluoro methyl)phenyl] 2-Methyloxirane-2-carboxamide (1) (unreacted compound (I)<0.50%].

Filter the reaction mixture over Nutsche Filter and wash with 10 L acetone. Acetone was later on recovered completely at 40-50° C. under vacuum until dryness. To this dried residue, 50 L DM water was added and stirred the solution for 4-5 hours at RT. About 25 L Toluene was added to this solution and stirred the reaction mixture for 10-12 hours. (Solid become free flowing in nature). The reaction mixture was filtered and washed with 10 L Toluene. The solid was dried for 6-7 hours under vacuum at 40-50° C. 7.0 kg solid was obtained; Yield—95.2%, Water content <0.5% w/w; Purity >99.0% by HPLC.

Charged 50 liters of acetic acid into GLR under stirring followed by addition of 5 Kg of N-[4-Cyano-3-(trifluoromethyl)phenyl]-3-[(4-fluorophenyl)sulfanyl]-2-hydroxy-2-methyl propanamide (2) at room temperature and stirred for about 20 min in order to obtain the clear solution. Raise the temperature to 40-45° C. under stirring and start slowly adding 18 liters of 30% solution of Hydrogen peroxide in about 5-6 hrs through addition tank and maintained the same temperature for 11-12 hours under stirring. Cool the reaction mixture to room temperature.

In another GLR, prepared the Sodium bi carbonate solution (35 Kg in 250 liter DM water), charged the reaction mass of the earlier reaction flask into this sodium bicarbonate solution in 5-6 hrs at RT and continued stirring for about 30 min. Add 75 liters of Ethyl acetate and stirred for further 30 minutes. Stopped stirring and allow the layers to settle for about 30 min. separated the organic ethyl acetate layer and the aqueous layer is collected separately.

Again charged the collected aqueous layer and extracted twice with 50 liters ethyl acetate and separated the Ethyl acetate layers. Combined all the ethyl acetate layer. Then gave three water wash (50 liter) and made the organic ethyl acetate layer moisture free by the addition of anhydrous sodium sulphate. Again charged the layer and added activated carbon and stir for 1-2 hours. Filtered through hyflow bed followed by recovery of ethyl acetate at 40-45° C. under vacuum till the solvent reached to a level of about ~1 ml/g. Subsequently, cooled the reaction mass to 0-5° C. and maintain this temperature for 2-3 hours. Centrifuged the solid material and finally wash with chilled Ethyl acetate (~1.0 L). Dried the material at 60-70° C. under vacuum for 8-10 hours.

4.2 Kg solid was obtained; Yield—84% w/w, Water content 0.07% w/w and Purity—99.81% by HPLC.

Stage C). Purification of Crude Bicalutamide

Charge filtered Ethyl acetate (2.75 L) into a clean reaction flask followed by addition of Bicalutamide crude (250 gram; as obtained from Stage B2) at room temperature under stirring. Raise the temperature of the mixture to 60-65° C. to get the clear solution.

Recover the ethyl acetate at 40-50° C. under vacuum until the solvent left is nearly 1.0-1.5 ml/g. Cool the reaction mixture to 0-5° C. under stirring and maintain for 2-3 hours.

Filter through Nutsche and wash with chilled ethyl acetate (150 mL). Dry the material 70-75° C. under vacuum for 12 hours.

Weight of Pure Bicalutamide ~230 gram; Yield ~92.0%; Water content ~0.12% w/w

HPLC purity ~99.8%;

Process related impurities A—nil %; B—nil %; C—nil % and D—nil %

Figure 4:
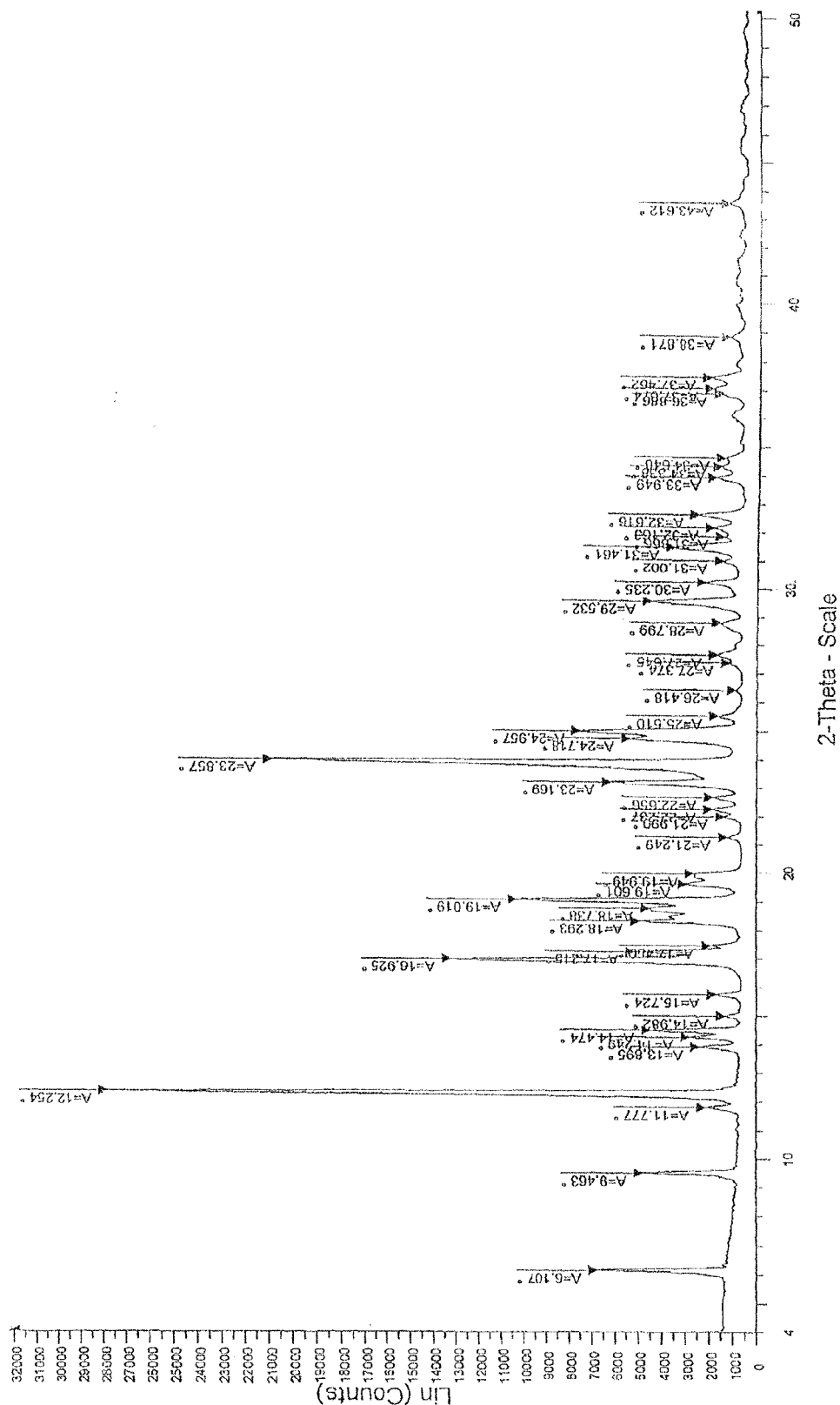
FIG. 4 is an example of a X-ray powder diffraction (XRPD) pattern of Bicalutamide, prepared according to Example-Stage-C.
Figure 5:
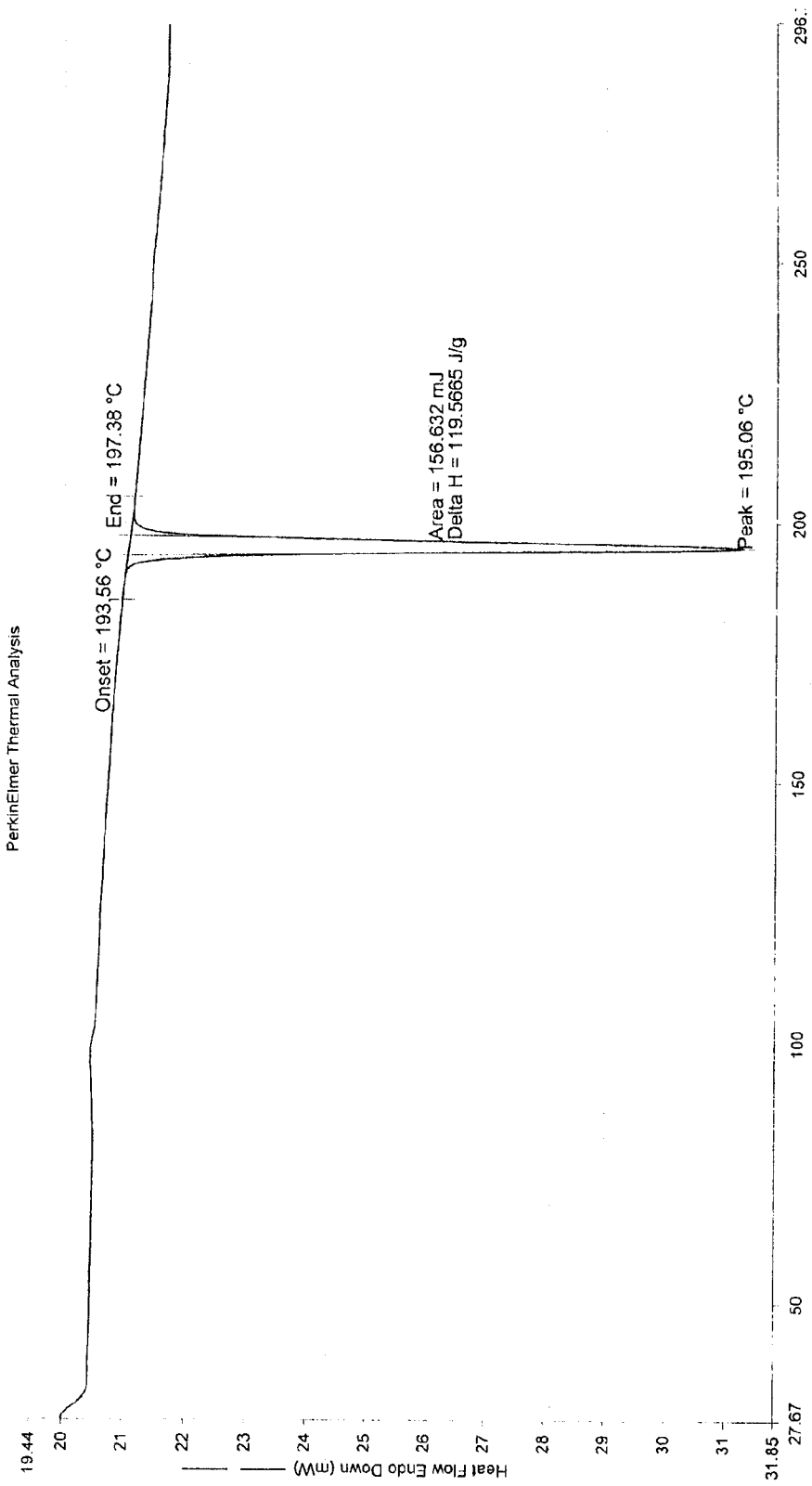
FIG. 5 is an example of a differential scanning calorimetry ("DSC') curve of Bicalutamide, prepared according to Example-Stage-C.
Figure 6:
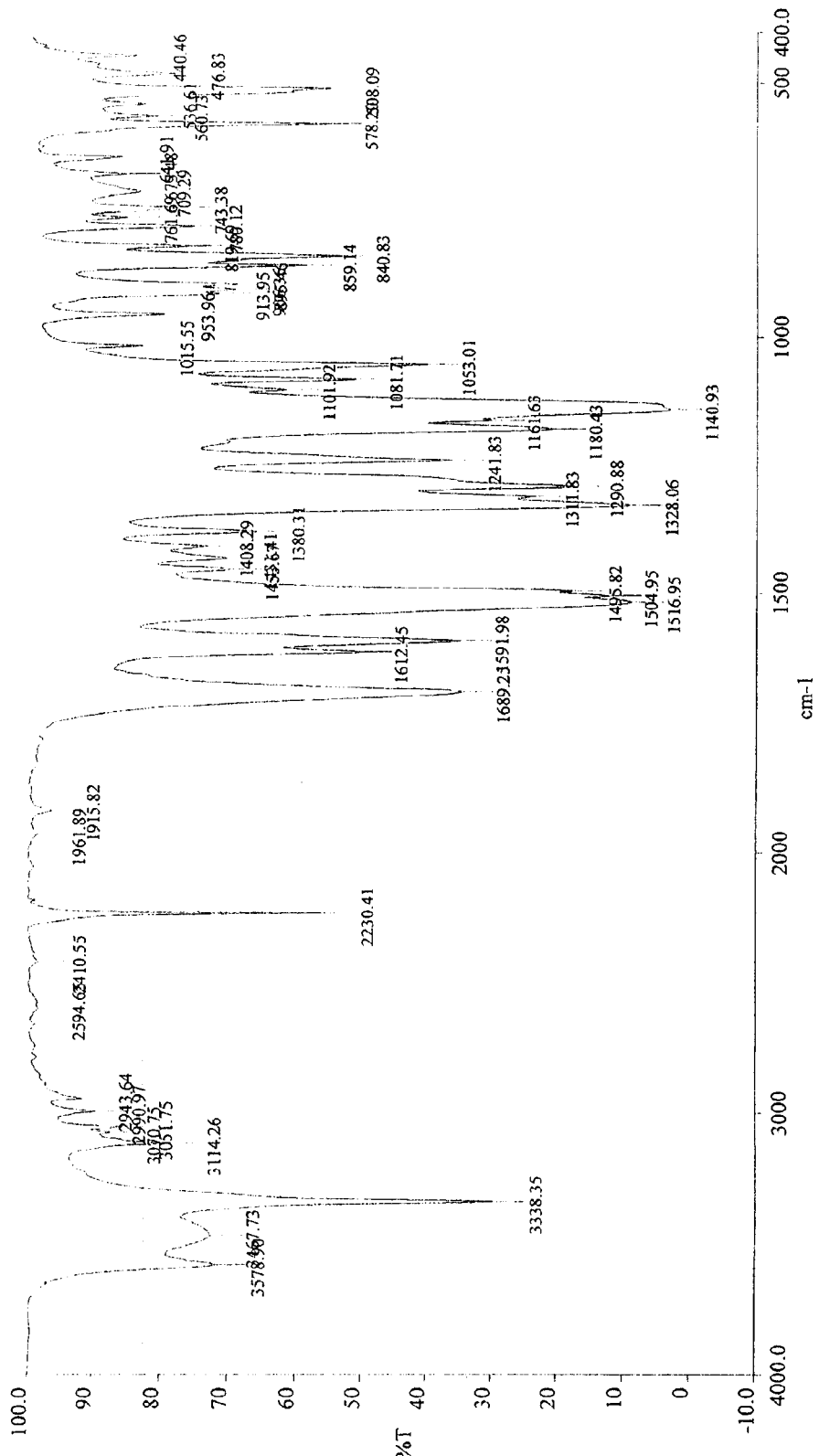
FIG. 6 is an example of FT-IR of Bicalutamide, prepared according to Example-Stage-C.

XRD as per FIG. 4
DSC Thermogram as per FIG. 5
IR Spectra as per FIG. 6

We claim:

1. A process of preparation of N-[4'-cyano-3'-(trifluoromethyl)phenyl]-3-[(4"-fluoro-phenyl)sulfonyl]-2-hydroxy-2-methylpropionamide (I)—

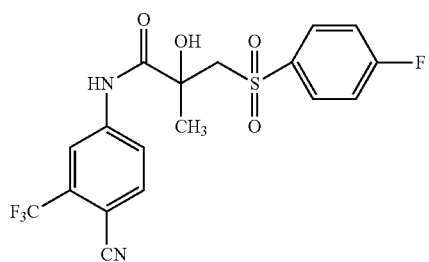

comprising the steps of
a. selectively oxidizing N-[4'-Cyano-3'-(trifluoromethyl) phenyl]-3-[(4"-fluoro phenyl)thio]-2-hydroxy-2-methyl propionamide of Formula (III)

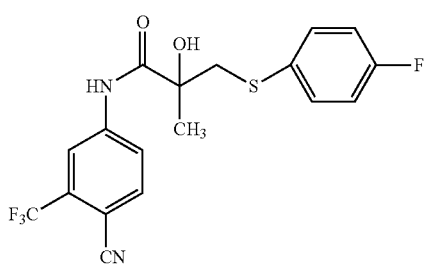

with 1% ortho tungstic acid and aqueous hydrogen peroxide in presence of an C1-C3 organic alcohol solvent;
b. raising the temperature to about 50° C. or more;
c. stirring until the content of compound of formula (III) achieved till less than about 1%;
c. isolating the solid by cooling the reaction mass;
d. adding mixture of water and water immiscible ester solvent (about 1:2);
e. separate the organic ester solvent layer;
f. optionally repeat the further extraction of aqueous layer with water immiscible ester solvent;
g. optionally adding activated carbon followed by filtering the extracted organic layer;
h. evaporating the water immiscible ester solvent; and
i. isolating the pure compound of formula (I).

2. The process according to claim 1, wherein the acid ester, is ethylacetate.

3. The process according to claim 1, wherein the oxidation is carried out at about 10° C.-30° C. in the presence of tungstic acid.

4. The process according to claim 1, wherein the optional purification is carried out in Ethyl acetate solvent.

5. The process according to claim 1, wherein crystalline N-[4'-cyano-3'-(trifluoromethyl)phenyl]-3-[(4"-fluoro-phenyl)sulfonyl]-2-hydroxy-2-methylpropionamide (I), obtained is substantially free from the process related impurities selected from A, B and/or C—

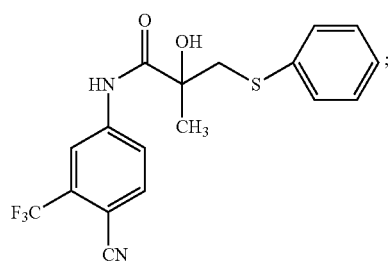

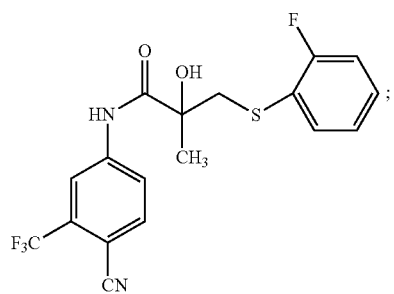

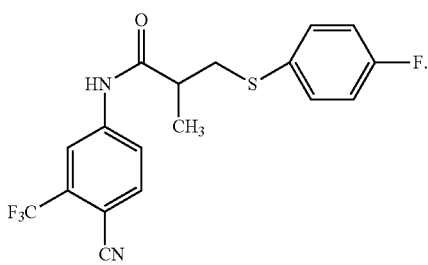

6. The process according to claim 1, wherein crystalline N-[4'-cyano-3'-(trifluoromethyl)phenyl]-3-[(4"-fluoro-phenyl)sulfonyl]-2-hydroxy-2-methylpropionamide (I) obtained is substantially free from impurities selected from A, B, C and/or D—

(A)

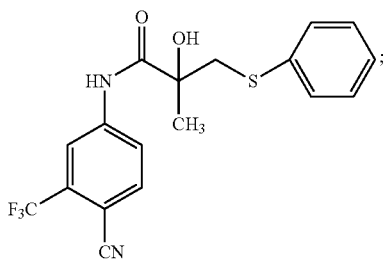

(B)

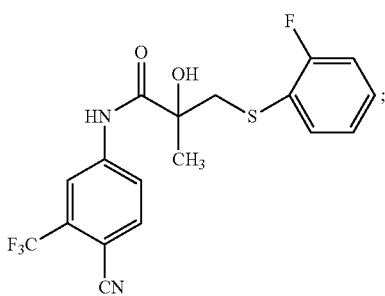

(C)

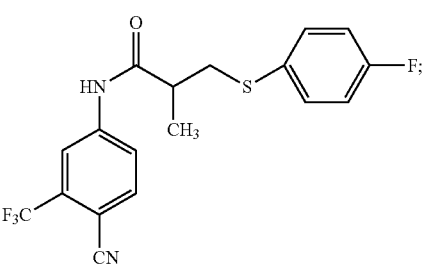

(D)

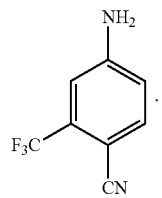

7. The process according to claim 4, wherein optional purification involves steps of purifying N-[4'-cyano-3'-(trifluoro methyl)phenyl]-3-[(4"-fluoro-phenyl)sulfonyl]-2-hydroxy-2-methylpropionamide (I) comprising mixing Bicalutamide with ethyl acetate and heating the solution containing Bicalutamide up to at least about 50° C. followed recovering ethyl acetate and isolating the product, substantially free from impurities A, B, C and D.

8. The process according to claim 1, wherein crystalline N-[4'-cyano-3'-(trifluoromethyl)phenyl]-3-[(4"-fluoro-phenyl)sulfonyl]-2-hydroxy-2-methylpropionamide (I) obtained has an X-ray diffraction pattern as per FIG. 1.

9. The process according to claim 1, wherein crystalline Bicalutamide obtained is designated as "Form-S" comprising an X-ray diffraction pattern having characteristic 2θ° and spacing values—6.1 (14.40 d value), 12.2 (7.20 d value), 16.9 (5.23 d value), 19.0 (4.65 d value), 23.8 (3.72 d value), 24.9 (3.56 d value), 29.5 and 31.5±0.2 (+0.1 d value).

\* \* \* \* \*